(12) United States Patent
Kanazawa (10) Patent No.: US 10,471,237 B2
(45) Date of Patent: Nov. 12, 2019

(54) GUIDE WIRE

(71) Applicant: ASAHI INTECC CO., LTD., Seto-shi, Aichi (JP)

(72) Inventor: Yuya Kanazawa, Seto (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 845 days.

(21) Appl. No.: 14/626,066

(22) Filed: Feb. 19, 2015

(65) Prior Publication Data

US 2015/0238734 A1   Aug. 27, 2015

(30) Foreign Application Priority Data

Feb. 24, 2014 (JP) ................. 2014-032993
Nov. 10, 2014 (JP) ................. 2014-228130

(51) Int. Cl.
*A61M 25/09* (2006.01)

(52) U.S. Cl.
CPC ... *A61M 25/09* (2013.01); *A61M 2025/09083* (2013.01); *A61M 2025/09091* (2013.01); *A61M 2025/09108* (2013.01); *A61M 2025/09175* (2013.01); *A61M 2025/09191* (2013.01)

(58) Field of Classification Search
None
See application file for complete search history.

(56) References Cited

U.S. PATENT DOCUMENTS

| | | |
|---|---|---|
| 3,452,742 A | 7/1969 | Muller |
| 4,854,330 A | 8/1989 | Evans, III et al. |
| 5,606,981 A * | 3/1997 | Tartacower ......... A61M 25/09 600/585 |
| 6,132,389 A * | 10/2000 | Cornish ............... A61M 25/09 600/585 |
| 8,585,613 B2 | 11/2013 | Nagano et al. |

(Continued)

FOREIGN PATENT DOCUMENTS

| | | |
|---|---|---|
| CN | 102727984 A | 10/2012 |
| EP | 2 005 988 A1 | 12/2008 |

(Continued)

OTHER PUBLICATIONS

Aug. 17, 2015 Extended Search Report issued in European Application No. 15156272.5.

(Continued)

*Primary Examiner* — Sean P Dougherty
*Assistant Examiner* — Benjamin S Melhus
(74) *Attorney, Agent, or Firm* — Oliff PLC (57) ABSTRACT

A guide wire includes a core shaft and a coil body covering an outer surface of a distal portion of the core shaft. The coil body includes a straight section that extends in a straight state from a proximal end of the coil body toward a distal end of the coil body, and a bent section arranged at a distal end of the straight section. The coil body may be formed by winding at least one element wire into a helical coil structure, or by winding a plurality of stranded wires (obtained by stranding a plurality of element wires) into a helical coil structure. The element wires and/or the stranded wires of the coiled body are in contact with each other on a side of the bent section opposite to a side toward which the bent section is bent relative to an axial direction of the straight section.

4 Claims, 7 Drawing Sheets

(56) References Cited

U.S. PATENT DOCUMENTS

| | | | |
|---|---|---|---|
| 2005/0154371 A1 | 7/2005 | Miyata et al. | |
| 2006/0264784 A1 | 11/2006 | Lupton | |
| 2007/0282225 A1* | 12/2007 | Terashi | A61M 25/09 600/585 |
| 2009/0005706 A1* | 1/2009 | Miyata | A61M 25/09 600/585 |
| 2010/0324539 A1 | 12/2010 | Lupton | |
| 2012/0253321 A1* | 10/2012 | Tsunezumi | A61M 25/09 604/528 |
| 2014/0142557 A1* | 5/2014 | Kosugi | A61M 25/09 606/1 |

FOREIGN PATENT DOCUMENTS

| | | |
|---|---|---|
| EP | 2 505 225 A2 | 10/2012 |
| JP | 2005-185386 A | 7/2005 |
| JP | 2007-501648 A | 2/2007 |
| JP | 2009-000337 A | 1/2009 |
| JP | 2012-005724 A | 1/2012 |
| JP | 2012-034967 A | 2/2012 |
| JP | 2012-205795 A | 10/2012 |
| JP | 1453479 | 10/2012 |
| JP | 2013-176488 A | 9/2013 |
| JP | 2014100300 A * | 6/2014 ............ A61M 25/09 |
| WO | 2005/014095 A1 | 2/2005 |

OTHER PUBLICATIONS

Design U.S. Appl. No. 29/499,555, filed Aug. 15, 2014 in the name of Kanazawa.
Design U.S. Appl. No. 29/500,813, filed Aug. 28, 2014 in the name of Kanazawa.
Jun. 30, 2017 Office Action issued in Japanese Patent Application No. 2014-228130.
Oct. 31, 2018 Office Action issued in Chinese Patent Application No. 201510043593.4.

* cited by examiner

GUIDE WIRE

CROSS-REFERENCE TO RELATED APPLICATIONS

This application claims priority to Japanese Application No. 2014-228130 filed on Nov. 10, 2014, and Japanese Application No. 2014-032993 filed on Feb. 24, 2014, the contents of which are incorporated by reference herein in their entirety.

BACKGROUND

The disclosed embodiments relate to a medical device. Specifically, the disclosed embodiments relate to a guide wire to be inserted into a body cavity for treatment or examination.

Various conventional medical devices are available for treatment or examination by insertion into a tubular organ (such as a blood vessel, a gastrointestinal tract, and a urinary duct), or into a body tissue. For example, Japanese Unexamined Patent Application Publication No. 2007-501648 discloses a guide wire including a core wire and a coil body covering an outer surface of a distal portion of the core wire. The coil body includes a straight section that extends distally in a straight state from the proximal end of the coil body, and a bent section arranged distally of the straight section.

In a condition known as chronic total occlusion (CTO), a blood vessel exhibits a relatively serious degree of stenosis. To treat the stenosis, it is preferable to bend the guide wire close to its distal end in order to allow the guide wire to pass through a slight gap in the stenosis portion, as performed in the guide wire described in Japanese Unexamined Patent Application Publication No. 2007-501648.

However, when the guide wire is bent in such a manner, a gap forms between element wires in the bent section. As a result, a fragment of a calcified lesion in the stenosis portion may enter the gap between element wires and interfere with the progression of the guide wire into the blood vessel. The guide wire will become stuck in the stenosis, decreasing the maneuverability of the guide wire as it passes through the stenosis portion.

Thus, because of the gap formed between element wires in the bent portion of the guide wire, even the guide wire described in Japanese Unexamined Patent Application Publication No. 2007-501648 may not be able to pass through the stenosis portion due to the interference between the bent section and the lesion. There is room for improvement in this regard.

SUMMARY

In view of the above aspects, the disclosed embodiments have been devised to provide a guide wire capable of preventing the distal portion of the guide wire from getting stuck in a stenosis portion of a tubular organ or a body tissue (e.g., a blood vessel), and to ensure that the guide wire can sufficiently pass through the stenosis portion.

In order to address the above problem, the guide wire according to the disclosed embodiments has the following characteristics.

A guide wire of the disclosed embodiments includes a core shaft and a coil body covering an outer surface of a distal portion of the core shaft. The coil body may be formed by winding a plurality of stranded wires (obtained by stranding a plurality of element wires) into a helical coil structure. The coil body includes a straight section extending in a straight state from a proximal end toward a distal end of the guide wire, and a bent section arranged at a distal end of the straight section. The stranded wires of the coil body are in contact with each other on an outer side of the bent section.

Ordinarily, if the element wires on the outer side of the bent section become separated from each other and form a space, a fragment of a calcified lesion in a stenosis portion, for example, may enter between the element wires and interfere with the progression of the guide wire into the blood vessel. The guide wire will then become stuck in the stenosis, decreasing the maneuverability of the guide wire as it passes through the stenosis portion. However, because the stranded wires on the outer side of the bent section are in contact with each other, the fragment of the lesion cannot enter between the stranded wires in the bent section. As a result, the distal portion of the guide wire will not get stuck, and the guide wire can pass freely through the stenosis portion.

In the guide wire of the disclosed embodiments, the coil body may be formed by winding a plurality of stranded wires into a helical coil structure. The wires are in close contact and press firmly against each other. Thus, even when the guide wire is bent to form the bent section, the wires do not separate from each other, and a gap is not formed. Therefore, it is possible to securely prevent a fragment of a lesion from entering the bent section.

Moreover, when stress is applied to the distal portion (the bent section) of the guide wire, slight relative movement is possible not only between stranded wires, but also between element wires forming the stranded wires. Thus, the distal portion has a high degree of freedom and excellent flexibility while being resistant to plastic deformation and securing a preferable restoring characteristic. Consequently, the guide wire can maneuver through a blood vessel and reach a selected target even in a blood vessel bent three-dimensionally in a complicated manner. Furthermore, even when the distal portion of the guide wire contacts a lesion having high hardness, the distal portion is not bent by stress exerted by the contact, and the guide wire can be used continuously.

In a guide wire of the disclosed embodiments, a winding angle of first stranded wires forming the bent section is larger than a winding angle of second stranded wires forming the straight section. In this manner, when the distal portion of the guide wire is bent, the first stranded wires forming the bent section are oriented in a vertical direction, and press against the second stranded wires forming the straight section in an axial direction. That is, it is possible to secure the contact between stranded wires even in a part where a gap would typically be easily generated between the stranded wires (i.e., at a boundary part between the straight section and the bent section) when the distal portion of the guide wire is bent.

In the guide wire, the first stranded wires forming the bent section are arranged substantially in parallel. This structure prevents a first stranded wire from sliding relative to an adjacent first stranded wire and separating therefrom, and no gap is generated between the stranded wires forming the bent section. This prevents a fragment of a lesion, for example, from entering between the stranded wires in the bent section. Thus, the distal portion of the guide wire will not get stuck, and the guide wire can pass freely through the stenosis portion.

Additionally, the first stranded wires forming the bent section are in pressure contact with each other. In this manner, it is possible to securely prevent a gap from forming between the stranded wires forming the bent section of the guide wire.

The straight section of the coil body may be tapered to a smaller diameter toward the bent section (the distal end). In this manner, the winding angle of the second stranded wires forming the straight section decreases toward the bent section, and the second stranded wires press against the first stranded wires forming the bent section. That is, the stranded wires are in pressure contact with each other at the border portion between the bent section and the straight section. As a result, it is possible to securely prevent a gap from forming between the stranded wires positioned at the border portion between the bent section and the straight section.

Moreover, the diameter of the coil body may be smallest at the proximal end of the bent section, which improves the flexibility of the bent section. Therefore, even in a blood vessel bent three-dimensionally in a complicated manner, the guide wire can sufficiently maneuver through the blood vessel and reach a selected target.

In addition, in the straight section of the guide wire, the diameter of the coil body may increase from the distal end to the proximal end of the straight section. Thus, when a press-in operation is performed, the sliding resistance to a blood vessel wall, for example, will increase toward the proximal end of the guide wire. Therefore, if the distal end (the bent section) of the guide wire penetrates through a blood vessel wall and projects outside the blood vessel and the operation is still continued thereafter, the sliding resistance of the straight section to the blood vessel wall (a wall of the through-hole) will gradually increase, thus conveying such touch feeling to a hand of an operator.

Consequently, it is easy to stop the press-in operation in the guide wire and introduce again the distal portion of the guide wire to a more appropriate blood vessel. That is, the distal portion of the guide wire can safely and accurately reach a target region.

The coil body may also be formed by winding at least one element wire into a helical coil structure. As in when stranded wires are used, the element wires on the outside of the bent section are in contact with each other. Ordinarily, if the element wires on the outer side of the bent section become separated from each another and form a space, a fragment of a calcified lesion in a stenosis portion, for example, may enter between the element wires and interfere with the progression of the guide wire into the tubular organ or body tissue. The guide wire will then become stuck in the stenosis, decreasing the maneuverability of the guide wire as it passes through the stenosis portion. However, because the element wires on the outer side of the bent section are in contact with each other, the fragment of the lesion cannot enter between the element wires in the bent section. As a result, the distal portion of the guide wire will not get stuck, and the guide wire can pass freely through the stenosis portion.

DETAILED DESCRIPTION OF EMBODIMENTS

A guide wire of the disclosed embodiments will be described with reference to the drawings. In the drawings, the left side corresponds to a distal end to be inserted into a body, while the right side corresponds to a proximal end to be operated by a technician such as a physician. Note that the dimensions in the drawings are not necessarily shown to scale.

Figure 1:
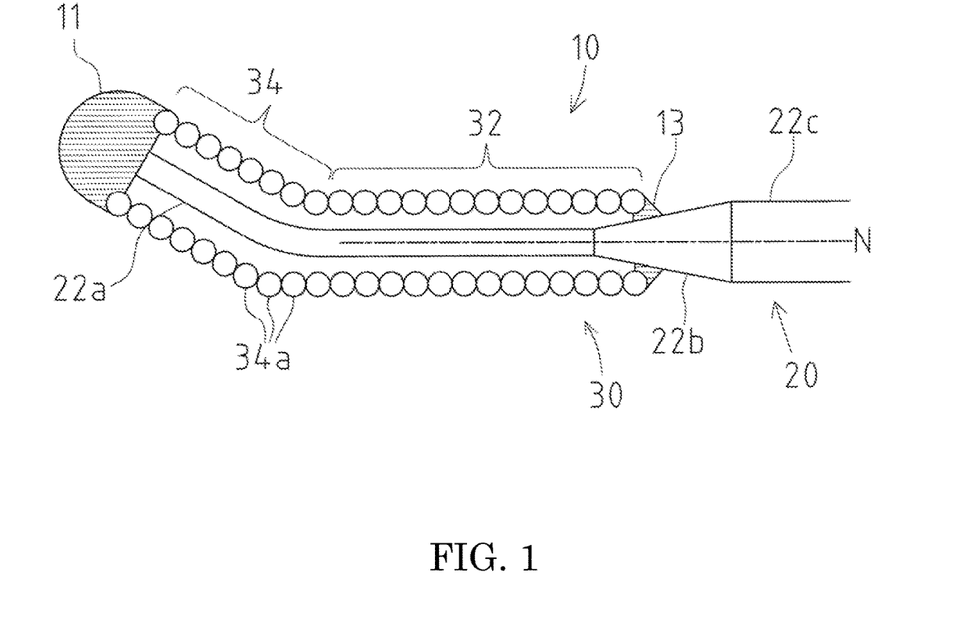
FIG. 1 is a partial cross-sectional enlarged view illustrating a guide wire of the disclosed embodiments.

FIG. 1 shows a guide wire 10 that may be used to facilitate positioning of a catheter in a cardiovascular system, for example. The guide wire 10 includes a core shaft 20 and a coil body 30 covering the outer periphery of a distal portion of the core shaft 20.

First, the core shaft 20 is described. The core shaft 20 includes a small diameter portion 22a, a tapered portion 22b, and a large diameter portion 22c in this order from the distal end to the proximal end of the core shaft. The small diameter portion 22a terminates at the distal end of the core shaft 20, and is the softest portion of the core shaft 20. The small diameter portion 22a is formed to have a flat plate shape by press working. The tapered portion 22b is tapered with a circular cross-section, and decreases in diameter toward the distal end. The large diameter portion 22c has a larger diameter than the small diameter portion 22a.

The material composing the core shaft 20 is not especially limited, and includes stainless steel (SUS304), a superelastic alloy such as a Ni—Ti alloy, a piano wire, or a cobalt alloy, for example.

Next, the coil body 30 is described. In the guide wire of FIG. 1, the coil body 30 is a single wound coil formed by winding an element wire into a helical coil structure.

As illustrated in FIG. 1, a distal end of the coil body 30 is fixed to the distal end of the core shaft 20 by a distal side joint portion 11. A proximal end of the coil body 30 is fixed to the core shaft 20 by a proximal side joint portion 13. The material composing the distal side joint portion 11 and the proximal side joint portion 13 is not especially limited, and includes a brazing metal such as a Sn—Pb alloy, a Pb—Ag alloy, a Sn—Ag alloy, or an Au—Sn alloy, for example.

The coil body 30 includes a straight section 32 that extends distally in a straight state from the proximal end of the coil body 30, and a bent section 34 arranged distally of the straight section 32. The bent section 34 is bent at a predetermined angle relative to an axial direction N of the straight section 32.

In FIG. 1, element wires 34a positioned on an outer side of the bent section 34 are in contact with each other. That is, there are no gaps between adjacent element wires 34a positioned on the outer side of the bent section 34.

Note that the outer side of the curved section 34 is a side opposite to the side toward which the bent section 34 is bent, relative to the axial direction N. This applies also to the guide wires described later.

Here, if the element wires 34a on the outer side of the bent section 34 were to become separated from each other and form a space, a fragment of a calcified lesion in a stenosis portion, for example, may enter between the element wires 34a and interfere with the progression of the guide wire into the blood vessel. The guide wire would become stuck in the stenosis, decreasing the maneuverability of the guide wire as it passes through the stenosis portion. However, because the element wires 34a on the outer side of the bent section 34 are in contact with each other, the fragment of the lesion cannot enter between the element wires 34a in the bent section 34. As a result, the distal portion of the guide wire 10 will not get stuck, and the guide wire can pass freely through the stenosis portion.

The material composing the coil body 30 is not especially limited, and the coil body 30 may be formed by a radiopaque element wire or a radiotransparent element wire. The material of the radiopaque element wire is not especially limited, and includes gold, platinum, tungsten, or an alloy including such elements (e.g., a platinum-nickel alloy), for example. The material of radiotransparent element wire is not especially limited, and includes stainless steel (SUS304, SUS316, etc.), a super-elastic alloy such as a Ni—Ti alloy, or a piano wire, for example.

Figure 2:
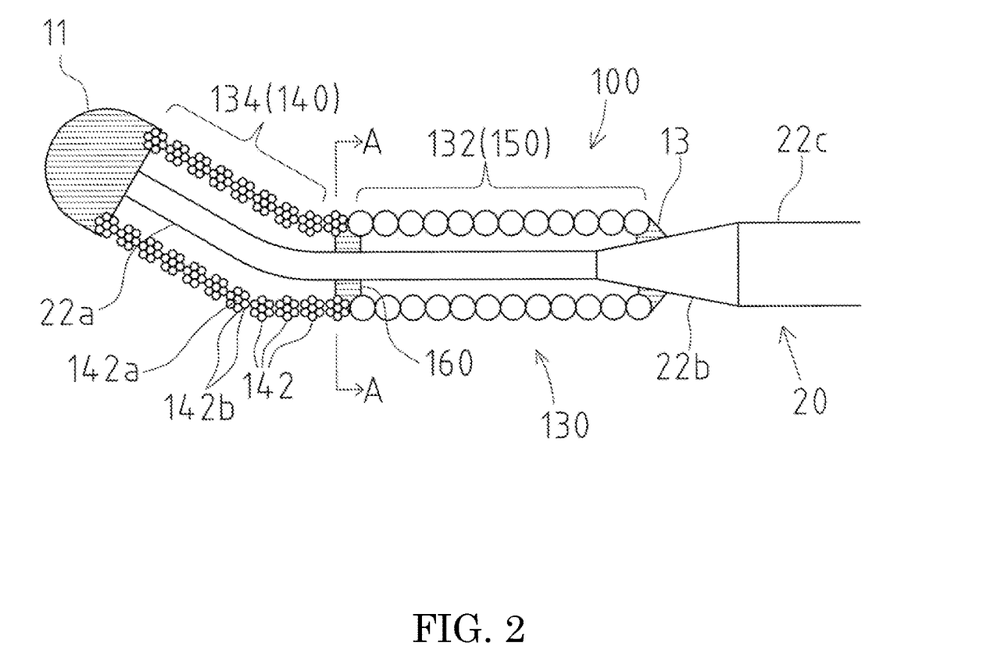
FIG. 2 is a partial cross-sectional enlarged view illustrating another guide wire of the disclosed embodiments.

FIG. 2 shows a guide wire 100 having a coil body 130 comprising a first coil portion 140 forming a bent section 134 and a second coil portion 150 forming a straight section 132. The first coil portion 140 forming the bent section 134 is formed by winding a plurality of stranded wires 142, which are obtained by stranding a plurality of element wires 142a, 142b, into a helical coil structure.

Figure 3:
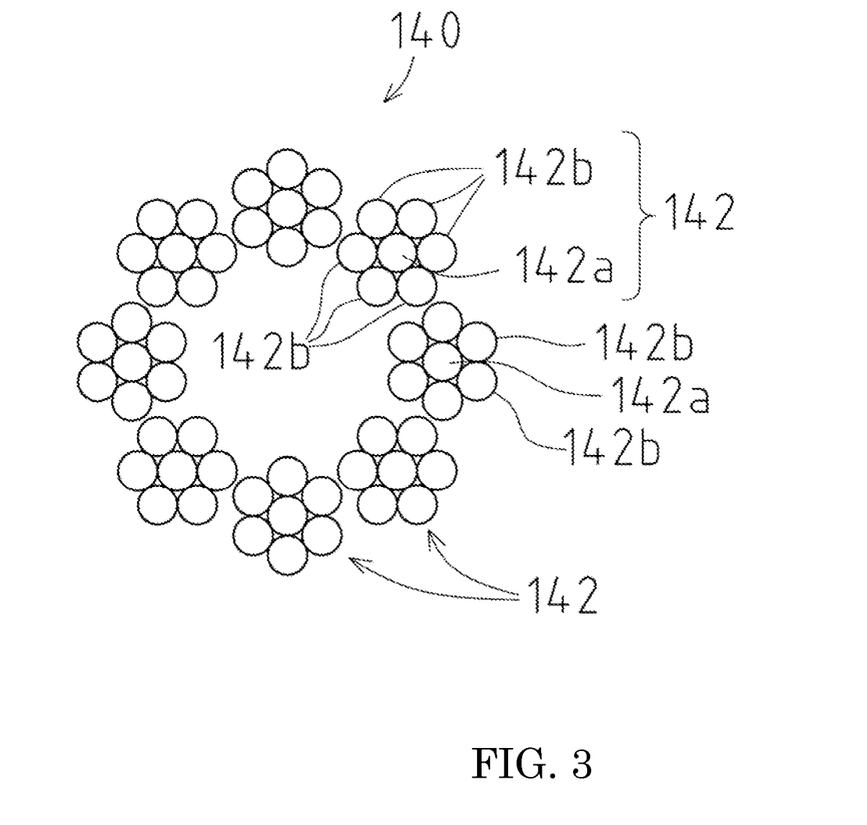
FIG. 3 is a cross-sectional view taken from A-A of a coil body in FIG. 2.

To be more specific, as illustrated in FIGS. 2 and 3, the first coil portion 140 forming the bent section 134 is formed by winding a plurality of the stranded wires 142 (here, eight stranded wires) into a helical coil structure. Each of the stranded wires includes a core element wire 142a and six side element wires 142b wound to cover the periphery of the core wire 142a.

The material composing the core element wire 142a and the side element wires 142b is not especially limited, and includes stainless steel such as martensitic stainless steel, ferritic stainless steel, austenitic stainless steel, austenite-ferrite duplex stainless steel, or a precipitation hardening type stainless steel; a super-elastic alloy such as a Ni—Ti alloy; or platinum, gold, tungsten, tantalum, iridium, or an alloy including such elements, which are radiopaque metals impermeable to radiation such as X-rays, for example.

As described above, in the guide wire 100, the first coil portion 140 forming the bent section 134 is formed by winding the stranded wires 142 (which are obtained by stranding the element wires 142a, 142b) into a helical coil structure. In the bent section 134 having such a structure, the stranded wires 142 are in close contact with each other. Thus, when the bent section 134 is formed, the stranded wires 142 do not separate from each other and a gap is not generated therebetween. This prevents a fragment of a lesion from entering between the stranded wires of the bent section 134. As a result, the distal portion of the guide wire 100 will not get caught, and the guide wire can pass freely through the stenosis portion.

When stress is applied to the distal portion (the bent section 134) of the guide wire 100, slight relative movement is possible not only between the stranded wires 142, but also between the element wires 142a, 142b forming the stranded wires 142. Thus, the distal portion has a high degree of freedom and excellent flexibility while being resistant to plastic deformation and securing a preferable restoring characteristic. Consequently, the guide wire can maneuver through a blood vessel and reach a selected target even in a blood vessel bent three-dimensionally in a complicated manner. Furthermore, even when the distal portion of the guide wire 100 contacts a lesion having high hardness, the distal portion is not bent by stress exerted by the contact, and the guide wire can be used continuously.

Meanwhile, the second coil body 150 forming the straight section 132 is formed by a single-wound coil obtained by winding an element wire into a helical coil structure. The material composing the second coil body 150 is not especially limited, and the second coil body may be formed by a radiopaque element wire or a radiotransparent element wire. The material of the radiopaque element wire is not especially limited, and includes gold, platinum, tungsten, or an alloy including such elements (e.g., a platinum-nickel alloy), for example. The material of the radiotransparent element wire is not especially limited, and includes stainless steel (SUS304, SUS316, etc.), a super-elastic alloy such as a Ni—Ti alloy, and a piano wire, for example.

A proximal end of the first coil portion 140 and a distal end of the second coil portion 150 are joined together by an intermediate joint portion 160. The material composing the intermediate joint portion 160 is not especially limited, and includes a brazing metal such as a Sn—Pb alloy, a Pb—Ag alloy, a Sn—Ag alloy, and an Au—Sn alloy, for example.

Figure 4:
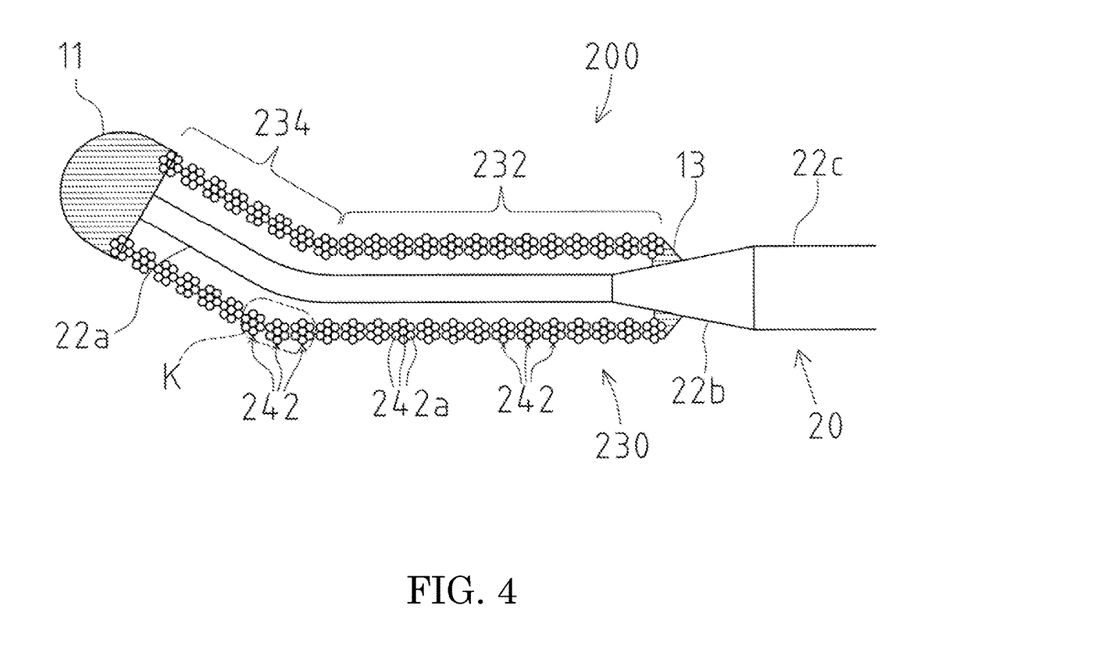
FIG. 4 is a partial cross-sectional enlarged view illustrating a guide wire of the disclosed embodiments.

FIG. 4 shows a guide wire 200 having both a curved section 234 and a straight section 232 that are formed by winding a plurality of stranded wires 242 into a helical coil structure. That is, the coil body 230 is configured entirely by winding a plurality of stranded wires 242 into a helical coil structure. Each stranded wire is obtained by stranding a plurality of element wires 242a. Note that the structure of the coil body 230 in FIG. 4 is same as the first coil portion 140 in FIG. 2 described above.

In this structure, the stranded wires 242 are in close contact with each other, and a gap is not generated when the guide wire is bent to form the bent section 234. In particular, the coil body 230 is formed entirely by winding a plurality of the stranded wires 242 into a helical coil structure, and thus the stranded wires positioned at a border portion K between the straight section 232 and the bent section 234 are in pressure contact with each other.

That is, even in a portion where a gap would typically be easily generated when the guide wire is bent to form the bent section 234 (i.e., at the border portion K between the straight section 232 and the bent section 234), it is possible to effectively prevent generation of a gap, and to securely prevent a fragment of a lesion, for example, from entering between the stranded wires 242. As a result, the distal portion of the guide wire 200 will not get stuck, and the guide wire 200 can pass freely through the stenosis portion.

Furthermore, in the proximal portion of the coil body 230 (the straight section 232), the element wires 242a press firmly against each other and the stranded wires 242 also press firmly against each other, which increases contact pressure and improves adherence of the stranded wires 242 and element wires 242a to each other even when a rotational force is applied. Consequently, torque transmission performance is improved, and the guide wire 200 can freely move through the blood vessel without getting stuck.

The structure of the bent section 234 and the vicinity thereof will be described in detail with reference to FIG. 5.

Figure 5:
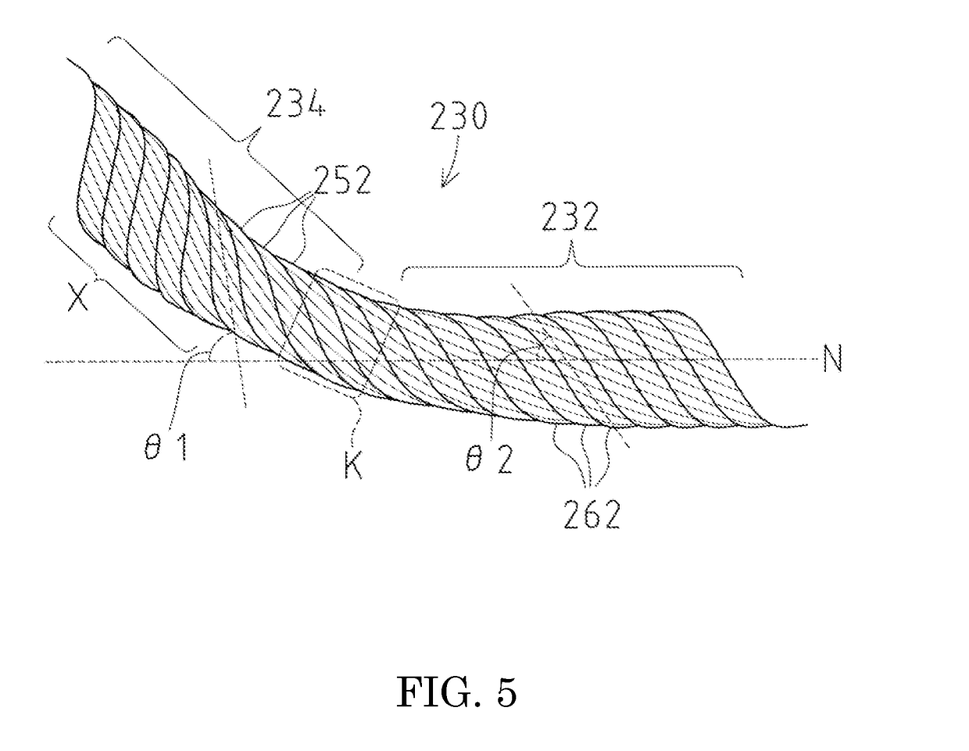
FIG. 5 is a partial enlarged view illustrating a bent section of a coil body in FIG. 4 and the vicinity thereof.

As illustrated in FIG. 5, a winding angle $\theta 1$ of the first stranded wires 252 forming the bent section 234 is larger than a winding angle $\theta 2$ of the second stranded wires 262 forming the straight section 232. In this manner, when the distal portion of the guide wire 200 is bent to form the bent section 234, the first stranded wires 252 forming the bent section 234 are oriented in a vertical direction, and press against the second stranded wires 262 forming the straight section 232 in an axial direction N.

Note that the winding angle θ1 of the first stranded wires 252 is an acute angle defined by the axial direction N of the straight section 232 and the winding direction of the first stranded wires 252, while the winding angle θ2 of the second stranded wires 262 is an acute angle defined by the axial direction N of the straight section 232 and the winding direction of the second stranded wires 262. This applies also in the guide wires described later.

That is, it becomes possible to secure contact between the stranded wires 252, 262 even in a portion where a gap would typically be easily generated when the distal portion of the guide wire 200 is bent (i.e., the border portion K between the straight section 232 and the curved section 234).

Furthermore, the first stranded wires 252 forming the bent section 234 are arranged substantially in parallel in a part X. This structure prevents a first stranded wire 252 forming the bent section 234 from sliding relative to an adjacent first stranded wire 252 and separating therefrom, and thus no gap is formed between the stranded wires 252 forming the bent section 234. This prevents a fragment of a lesion from entering between the first stranded wires 252 forming the bent section 234. Thus, the distal portion of the guide wire 200 will not get stuck, and the guide wire 200 can pass freely through the stenosis portion.

Moreover, in the bent section 234, the adjacent first stranded wires 252 are in pressure contact with each other. In this manner, it is possible to securely prevent generation of a gap between the first stranded wires 252 forming the bent section 234 of the guide wire 200.

Figure 6:
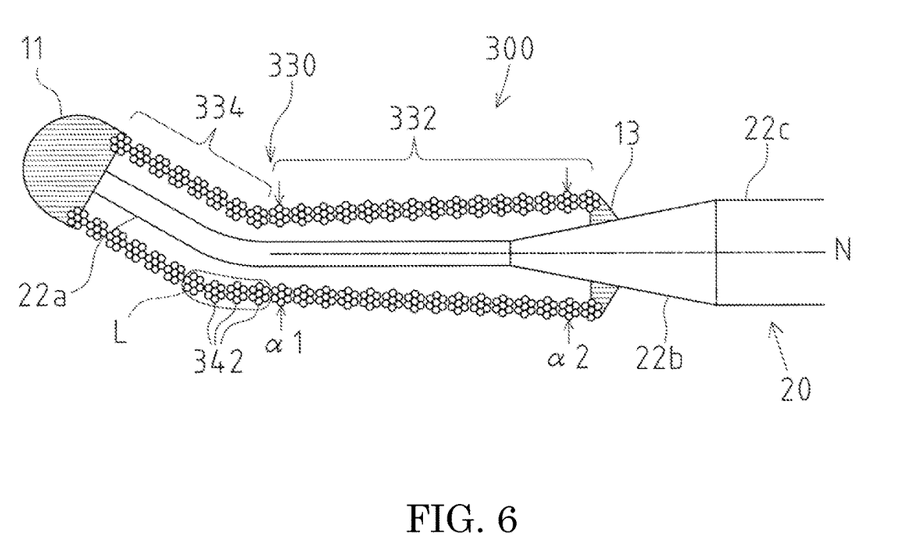
FIG. 6 is a partial cross-sectional enlarged view illustrating another guide wire of the disclosed embodiments.

FIG. 6 shows a guide wire 300 in which a straight section 332 of a coil body 330 is tapered to a smaller diameter toward a bent section 334 (the distal end). That is, in the straight section 332, an outer diameter α1 at a distal end of the straight section 332 is smaller than an outer diameter α2 at a proximal end of the straight section 332.

Figure 7:
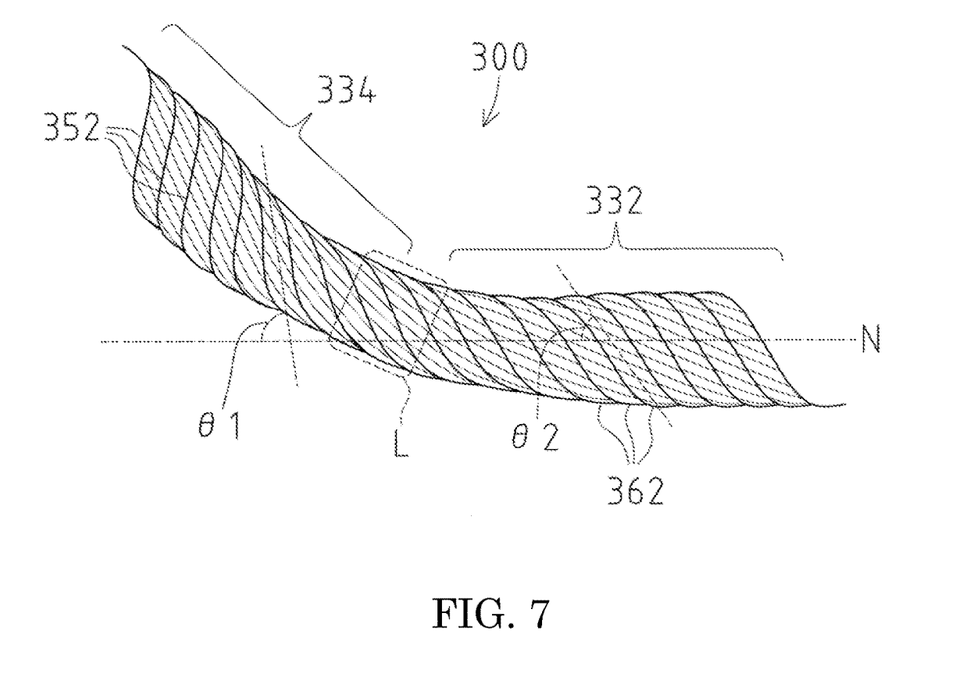
FIG. 7 is a partial enlarged view illustrating a bent section of a coil body in FIG. 6 and the vicinity thereof.

In this manner, the winding angle θ2 of the second stranded wires 362 forming the straight section 332 gradually decreases toward the distal end of the straight section 332, and the second stranded wires 362 press in the distal direction against the first stranded wires 352 forming the bent section 334, as illustrated in FIG. 7.

That is, as illustrated in FIGS. 6 and 7, the stranded wires 352, 362 are in pressure contact with each other at a border portion L between the bent section 334 and the straight section 332. As a result, it is possible to securely prevent a gap from forming between the stranded wires 342 (352, 362) even in a portion where a gap would typically be easily generated when the distal portion of the guide wire 300 is bent (i.e., the border portion L between the straight section 332 and the bent section 334).

Moreover, in FIG. 6, the outer diameter of the coil body is smallest at the proximal end of the bent section 334, which improves flexibility of the curved section 334. Thus, even in a blood vessel bent three-dimensionally in a complicated manner, the guide wire 300 can sufficiently maneuver through the blood vessel and reach a selected target.

In addition, in the straight section 332 of the guide wire 300, the diameter increases from the distal end to the proximal end of the straight section. Thus, when a press-in operation is performed, sliding resistance to a blood vessel wall, for example, will increase toward the proximal end of the guide wire. Thus, if the distal portion (the bent section 334) of the guide wire 300 penetrates through a blood vessel wall and projects outside the blood vessel and the operation is still continued thereafter, the sliding resistance of the straight section 332 to the blood vessel wall (a wall of the through-hole) will gradually increase, thus conveying such touch feeling to a hand of an operator.

Consequently, it is easy to stop a press-in operation in the guide wire 300 and introduce again the distal portion of the guide wire 300 to a more appropriate blood vessel. That is, the distal portion of the guide wire 300 can safely and accurately reach a target region. Furthermore, by using a coil body 330 whose outer diameter becomes smaller toward the distal end, the sliding resistance to a blood vessel wall, for example, during a press-in operation will increase toward the proximal end, thus easily conveying touch feeling in the guide wire to a hand of an operator during the press-in operation.

What is claimed is:

1. A guide wire comprising:
a core shaft; and
a coil body covering an outer surface of a distal portion of the core shaft,
wherein:
the coil body is formed by winding a plurality of stranded wires into a helical coil structure, each of the plurality of stranded wires being obtained by stranding a plurality of element wires,
the coil body includes a straight section that extends in a straight state from a proximal end of the coil body toward a distal end of the coil body, and a bent section arranged at a distal end of the straight section,
first stranded wires form the bent section and second stranded wires form the straight section,
a winding angle of the first stranded wires is larger than a winding angle of the second stranded wires so that the stranded wires are in firmer contact with each other on a first side of the bent section than in the straight section, the first side being opposite to a second side facing a bending direction toward which the bent section is bent relative to an axial direction of the straight section, and
the winding angle of the first stranded wires is a first acute angle defined by a longitudinal axis of the straight section and a winding direction of the first stranded wires, and the winding angle of the second stranded wires is a second acute angle defined by the longitudinal axis of the straight section and a winding direction of the second stranded wires.

2. The guide wire according to claim 1, wherein an outer diameter of the bent section is smaller at a proximal end of the bent section than at a distal end of the bent section.

3. The guide wire according to claim 1, wherein the straight section is tapered to a smaller diameter toward the distal end of the straight section.

4. The guide wire according to claim 2, wherein the straight section is tapered to a smaller diameter toward the distal end of the straight section.

* * * * *